United States Patent [19]

Zeeck et al.

[11] Patent Number: 4,939,125

[45] Date of Patent: Jul. 3, 1990

[54] ACYL DERIVATIVES OF URDAMYCIN A, THEIR PREPARATION AND THEIR USE

[75] Inventors: Axel Zeeck; Thomas Ciesiolka, both of Göttingen; Hans Zähner, Tübingen; Hannelore Drautz, Mössingen, all of Fed. Rep. of Germany

[73] Assignee: Hoechst Aktiengesellschaft, Frankfurt am Main, Fed. Rep. of Germany

[21] Appl. No.: 89,442

[22] Filed: Oct. 5, 1987

[30] Foreign Application Priority Data

Aug. 28, 1986 [DE] Fed. Rep. of Germany ....... 3629273

[51] Int. Cl.$^5$ .................... A61K 31/71; C07H 15/24
[52] U.S. Cl. ......................... 514/34; 514/25; 514/908; 536/6.4; 536/16.8; 536/18.1; 435/74; 435/78; 435/896
[58] Field of Search ................. 514/33, 34, 25, 908; 536/16, 8, 16.9, 18.1, 18.2, 6.4; 435/74, 896, 78

[56] References Cited

U.S. PATENT DOCUMENTS 4,859,655 8/1989 Zeeck et al. .................... 514/34

FOREIGN PATENT DOCUMENTS 3441933 6/1986 Fed. Rep. of Germany.

OTHER PUBLICATIONS

Zeeck et al.; Chemical Abstracts 106: 48630q, Jun. 5, 86.
Rohr et al.; J. Antibiotics 40(4): 459–67, (1987).
Drautz et al.; J. Antibiotics 39(12): 1657–69, (1986).
Salmon et al.; New England Journal of Medicine, 298: 1321–1327, (1978).

*Primary Examiner*—Ronald W. Griffin
*Assistant Examiner*—Nancy S. Carson
*Attorney, Agent, or Firm*—Finnegan, Henderson, Farabow, Garrett and Dunner

[57] ABSTRACT

The O-acyl derivatives of urdamycin A exhibit an antibiotic or antitumoral activity.

5 Claims, No Drawings

ACYL DERIVATIVES OF URDAMYCIN A, THEIR PREPARATION AND THEIR USE

Urdamycins A to F and their aglycones, the corresponding urdamycinones, are described in German Offenlegungsschrift 3,441,933, which is equivalent to U.S. patent application Ser. No. 798,571. Urdamycins are prepared by fermentation with a microorganism strain which has been isolated from a soil sample from Tanzania. The microorganism has been identified as Streptomyces fradiae and filed in the Deutsche Sammlung von Mikroorganismen (DSM) [German Register of Microorganisms] under the number DSM 3093. Urdamycinones can be obtained by acid hydrolysis or methanolysis of urdamycins. The known urdamycins and urdamycinones have an antibacterial and tumor-inhibiting action and can thus be used in the form of pharmaceutical preparations for treatment of bacterial infections or for treatment of tumor disorders in humans and animals.

It has now been found that acyl derivatives of urdamycin A likewise have an antibiotic action and an antitumoral activity. Compared to the known urdamycins and urdamycinones, these new derivatives surprisingly have a greater activity.

The invention thus relates to:
1. The compound of the general formula I

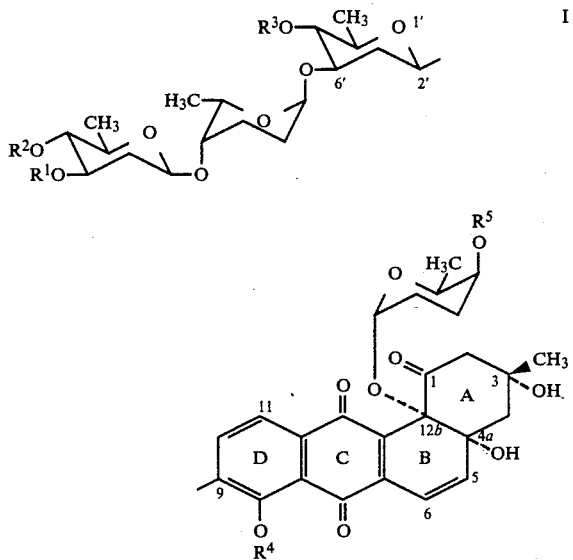

having at least one acyl group, in which $R^1$ to $R^5$, independently of one another, are hydrogen or a $(C_1-C_{18})$-acyl group, apart from 5',3B,4B,4C,8-penta-O-acetylurdamycin A.

2. The process for the preparation of the compound of the general formula I having at least one acyl group, apart from penta-O-acetylurdamycin A, wherein urdamycin A is acylated.

3. The use of the compound of the general formula I for the preparation of medicaments.

The invention is described below in detail, in particular in its preferred embodiments, and is defined in the patent claims.

In the compound of the general formula I, $R^1$ to $R^5$ can denote hydrogen or a $(C_1-C_{18})$-acyl group which is derived from an organic carboxylic acid. The latter contains straight-chain, branched or cyclic aliphatic, aliphatic-aromatic or aromatic hydrocarbon radicals which are themselves unsubstituted or substituted by halogen, for example chlorine or bromine, or esterified or etherified hydroxyl groups. The $(C_1-C_{10})$-acyl compound is preferably prepared, in particular the acetyl compound. Urdamycin A, which can be obtained according to Example 1, is in this case treated with an acylating agent which introduces the corresponding acyl radicals of an organic carboxylic acid. In this case, the appropriate carboxylic acid or a reactive derivative, in particular an anhydride, is used. The acylation can be carried out in the presence of suitable condensing agents, for example in the presence of carbodiimide compounds, such as dicyclohexylcarbodiimide, or carbonyl compounds, such as diimidazolylcarbonyl, when free carboxylic acids are used, and, for example, in the presence of basic agents, such as tri(lower alkyl)amine, for example triethylamine, or heterocyclic bases, for example pyridine or 4-dimethylaminopyridine, or basic salts, for example anhydrous sodium acetate, when reactive carboxylic acid derivatives are used.

The acylation reaction can be carried out in the absence or in the presence of a solvent or mixture of solvents with cooling, at room temperature or with warming, and, if necessary, in a closed vessel and/or in an inert gas, for example nitrogen, atmosphere. Suitable solvents are, for example, simple or substituted, for example chlorinated, aliphatic, cycloaliphatic or aromatic hydrocarbons, it being possible to use suitable esterification reagents, such as acetic anhydride, or alternatively suitable bases, such as pyridine, as diluents. By choosing appropriate reaction conditions, the synthesis of certain acyl compounds can be controlled in a specific fashion. This is achieved, for example, by varying the base, the reaction temperature or the reaction time or by varying several parameters simultaneously.

However, the reaction is preferably carried out using an anhydride, in particular acetic anhydride, in the presence of pyridine or sodium acetate. The reaction temperatures and the reaction times are between $-10°$ and $+100°$ C. and 2 minutes and 48 hours, preferably between $20°$ and $30°$ C. and 8 minutes and 16 hours. The anhydride: base ratio is in the range from 20:1 to 1:1, preferably 2:1. The concentration of urdamycin A in the reaction batch is between 0.05–10%, preferably 0.1–1%.

When the reaction is complete, the reaction product can be isolated by extraction. For further purification, it is then chromatographed, for example on silica gel.

Alternatively, mono- to tetraacyl compounds can be prepared by basic acyl cleavage of 5',3B,4B,4C,8-penta-O-acylurdamycin A. Bases such as the alkali metal or alkaline-earth metal hydroxides or alkali metal carbonates are used in aqueous/alcoholic solution at $-10°$ to $+100°$ C. The acyl cleavage is preferably carried out in aqueous/methanolic solution at $25°$ C. using a saturated sodium carbonate solution. Subsequent work-up is carried out as described above.

The invention is described in further detail in the following examples. Unless otherwise stated, percentage data refer to the weight.

EXAMPLES

1. Preparation of 5',3B,4B,8-tetra-O-acetylurdamycin A

Urdamycin A is prepared in the following steps:
(a) Preparation of a spore suspension of the producer strain:

100 ml of nutrient solution (4 g of yeast extract, 10 g of malt extract, 4 g of glucose and 1 liter of tap water, pH before sterilization 7.3, 20 g of agar for solidification) in a 500 ml conical flask with a lateral injection port are inoculated with the strain DSM 3093 and incubated at 27° C. and 120 rpm on a rotating shaking machine for 72 hours. 20 ml of culture liquid are then uniformly distributed on to 50 ml of agar in the 500 ml conical flask and decanted. The cultures are incubated at 27° C. for 10–14 days. The spores of one flask formed after this time are floated off with 500 ml of deionized water containing one drop of commercially available non-ionic surfactant and kept at −22° C.

(b) A 500 ml conical flask with a lateral injection port and 100 ml of a nutrient solution with a composition of 2% of meat meal, 10% of malt extract, 1% of calcium carbonate and water to 100% (pH 7.2 before autoclaving) is inoculated with a culture grown on a slant tube or with 0.2 ml of spore suspension and the mixture is incubated on a shaking machine at 120 rpm and 27° C. The maximum antibiotic production is reached after 72 hours. A submerged culture (5%) 48 hours old, from the same nutrient solution is sufficient for innoculation of 10, 20, 25 and 100 liter fermenters.

(c) A fermenter with a capacity of 10 liters is operated under the following conditions: 4 liters of air per minute are passed into the culture liquid (medium as in subparagraph a) at an incubation temperature of 27° C. and a stirrer speed of 250 rpm. Foam can be suppressed by repeated addition of a few drops of ethanolic polyol solution. The production maximum is reached after about 48 hours. The yields are about 10 mg/l urdamycin A.

(d) Urdamycin A can also be isolated as follows: A culture broth obtained according to one of the preceding methods is filtered through a filter press with the addition of 2% of filtration aid (diatomaceous earth). The mycelium, which has only a slight antibiotic activity, is discarded. The culture filtrate is extracted exhaustively with ethyl acetate at pH 7. The organic phase is dried and evaporated. A copious amount of petroleum ether is poured over the oily evaporation residue. The precipitate which has separated out is centrifuged off and dried and further processed as urdamycin crude product.

The crude product is chromatographed on a silica gel column (silica gel 60, less than 0.08 mm) using chloroform methanol (4:1). The following fractions are eluted in succession, one of the urdamycins being chiefly enriched in each fraction:

Fraction 1 (yellow): urdamycin B
Fraction 2 (red): urdamycin E
Fraction 3 (yellow-red): urdamycin A
Fraction 4 (blue): urdamycin D
Fraction 5 (red): urdamycin C
Fraction 6 (orange): urdamycin F (e) Fraction 3 (urdamycin A) is subsequently purified on a silica gel column with methylene chloride/ethanol (9:1) and then on a column of SEPHADEX LH 20 in methanol. The urdamycin A eluted in each case from the main zone is finally dissolved in a little acetone and precipitated by dropwise addition of this solution into a 20-fold excess of n-hexane. The yellow-red solid thus obtained decomposes at 160° C. and has the following properties:

Circular dichroism spectrum in methanol: $max[\theta]^{24)}=456$ (+5000), 400 (−9000), 328 (+35000), 290 sh (+1100), 261 (−5000) and 232 nm (+38000).

Elemental analysis of the urdamycin A dried at 60° C. under a high vacuum gives C=60.47%, H=6.66%, no nitrogen or sulfur detectable.

Molecular weight: 845 according to FAB mass spectrum (negative ions).

The electron spectrum shows the following maxima:
Ethanol (yellow-red): $\lambda_{max}$ ($\Sigma$)=440 sh (5400), 426 (5500) and 319 nm (4500).

Ethanol/NaOH (ultramarine blue): $\lambda_{max}$ 580 (5400), 404 (1700) and 325 nm (8100).

IR (KBr): 3430; 1728; 1657 sh; 1650; 1639, 1620 and 1580$^{-1}$.

UV (ethanol): $\lambda_{max}$($\Sigma$)=440 sh (5400); 426 (5500) and 319 (4500) nm.

(ethanol/HCl): $\lambda_{max}$ ($\Sigma$)=as ethanol (ethanol/NaOH): $\lambda_{max}$ ($\Sigma$)=580 (5400); 404 (1700) and 325 (8100) nm.

$^1$H-NMR (200 MHz, d$_6$-acetone): $\delta$=0.51 (d, J=6.5 Hz, 5C-CH$_3$) 1.16 (d, J=6.5 Hz, 5A-CH$_3$); 1.17 (s, 3-CH$_3$); 1.24 (d, J=6 Hz, 5B-CH$_3$); 1.33 (o, J=3×about 12 Hz, 3'-H$_a$); 1.38 (d, J=6 Hz, 6'-CH$_3$); 1.4–2.0 (complex, 8H, 2C-H$_2$, 3C-H$_2$, 2A-H$_2$, 3A-H$_2$); 1.95 and 2.04 (dd and d, J=15 and 2 or 15 Hz, 4-H$_2$); 2.20 (o, J=13, 5, 2 Hz, 3'-H$_e$); 2.37 (o, J=13, 12, 12 Hz, 2B-H$_a$); 2.55 (o, J=13, 5, 2 Hz, 2B-H$_e$); 2.56 and 2.90 (dd and d, J=13, 2 or 13 Hz, 2-H$_2$); 2.94 (o, J=9, 9, 4 Hz, 5'-H); 3.19 (o, J=9, 9, 4 Hz, 4B-H); 3.27 (dq, J=9 and 6 Hz, 5B-H); 3.28 (o, J=3×2 Hz, 4C-H); 3.53 (dq, J=9 and 6 Hz, 6'-H); 3.56 (m, 3B-H); 3.58 (o, J=3×about 2 Hz, 4A-H); 3.68 (dq, J=6.5 and 2 Hz, 5C-H); 3.81 (s, OH*); 3.82 (o, J=12, 9, 5 Hz, 4'-H); 4.03 (d, J=5 Hz, OH*); 4.09 (d, J=5 Hz, OH*); 4.24 (dq, J=6, 5 and 2 Hz, 5A-H); 4.42 (s, OH*); 4.63 (d, J=4 Hz, OH*); 4.64 (dd, J=10 and 2 Hz, 1B-H); 4.93 (dd, J=10 and 2 Hz, 2'H); 5.02 (d, J=2 Hz, 1A-H); 5.32 (d, J=3 Hz, OH*); 5.33 (d, J=2 Hz, 1C-H); 6.53 (d J=10 Hz, 5-H); 6.93 (d, J=10 Hz, 6-H); 7.68 (d, J=8 Hz, 10-H); 7.99 (d, J=8 Hz, 11-H); and 12.38 (s, 8-OH*) ppm.

*Signals disappear after exchange with CD$_3$OD
**Signals become dd, J=9 and 9 Hz after CD$_3$OD exchange (200 MHz, d$_6$-DMSO): $\delta$=0.38 (d, J=6.5 Hz, 5C-CH$_3$); 1.04 (d, J=6.5 Hz, 5A-CH$_3$); 1.08 (s, 3-CH$_3$); 1.14 (d, J=6 Hz, 5B-CH$_3$); about 1, 2 (masked 3'-H$_a$); 1.3–1.8 (complex, 8H, 2C-, 3C-, 2A- and 3A-H$_2$); 1.75 and 1.86 (2d, J=15 Hz each, 4-H$_2$); 2.00 (o, J=13, 5, 2 Hz, 3'-H$_e$); 2.14 (o, J=13, 10, 10 Hz, 2B-H$_a$); 2.39 and 2.74 (2d, J=13 Hz each, 2-H$_2$); about 2, 5 (masked 2B-H$_e$); 2.72 (dd, J=2×10 Hz, 5'-H); 3.04 (dd, J=2×10 Hz, 4B-H); 3.10 (dq, J=10 and 6 Hz, 5B-H); 3.22 (o, J=12, 9, 5 Hz, 4'-H); 4.13 (dq, J=6.5 and 2 Hz, 5A-H); 4.30 (d, J=6 Hz, OH*); 4.47 (dd, J=10 and 2 Hz, 1B-H); 4.82 (dd, J=10 and 2 Hz, 2'-H); 4.84 (d, J=5 Hz, OH*); 4.85 (s, 1A-H); 4.90 (d, J=6 Hz, OH*); 5.10 (s, OH*); 5.11 (d, J=5 Hz, OH*); 5.12 (s, 1C-H); 5.65 (s, OH*); 6.39 (d, J=10 Hz, 5-H); 6.73 (d, J=10 Hz, 6-H); 7.55 (d, J=8 Hz, 10-H); 7.84 (d, J=8 Hz, 11-H); and 12.26 (s, 8-OH*) ppm.

*Signals disappear after exchange with D$_2$O.

CD (methanol): $\lambda_{extr.}$ ($\theta^{24}\times10^{-4}$)=456 (+0.5); 400 (−0.9); 328 (+3.5); 290 sh (+1.1); 261 (−0.5) and 232 (+3.8) nm.

$\alpha_D 24$ (c=0.1 acetone); +32°.

129 mg of urdamycin A thus obtained were dissolved in 22.5 ml of a mixture of acetic anhydride/pyridine in the ratio 2:1 and stirred at room temperature for 7 hours. The mixture was subsequently poured onto ice and extracted 3 times with chloroform, and the extract was evaporated to dryness. Traces of pyridine were removed by taking up several times in toluene with subsequent evaporation. The residue was chromatographed on silica gel (silica gel 60 below 0.08 mm, Macherey-Nagel) (2×30 cm column, chloroform/methanol 100:2; v:v). Besides 148 mg (92%) of 5′,3B,4B,4C,9-penta-O-acetylurdamycin A, 11 mg (6%) of the acetyl compound desired were obtained as a yellow solid, which was characterized as follows:

$C_{51}H_{64}O_{21}$ (1013.1)

Melting point: 160° C. (decomposition)

IR (KBr): 3450; 2980; 2938; 2870; 1781; 1745; 1664; 1632; 1598; 1561 cm$^{-1}$.

UV (methanol): $\lambda_{max}$ ($\epsilon$)=360 (4770); 313 sh (5510); 257.7 (15280) nm.

UV (methanol/HCl): $\lambda_{max}$ ($\epsilon$)=as methanol.

UV (methanol/NaOH): $\lambda_{max}$ ($\epsilon$)=401 (3140); 315.7 (7660); 255 (12560); 224 (16980) nm.

$^1$H NMR (200 MHz, CDCl$_3$): see Table 1.

CD (methanol): $\lambda_{extr.}$ ($\theta^{20} \times 10^{-3}$)=401 (−5.1); 318 (9.7); 288 (7.9); 267 (1.0); 232 (18.0) nm.

2. Preparation of 3B,4B,8-tri-O-acetylurdamycin A 25 mg of urdamycin A were dissolved in 7.5 ml of a mixture of acetic anhydride/pyridine (2:1), and the mixture was stirred at room temperature for 8 minutes, the color of the solution changing from orange to yellow. Since all the urdamycin A had reacted (TLC), the mixture was poured onto ice and extracted twice with 30 ml of chloroform in each case. The extracts were evaporated to dryness, and traces of pyridine were removed by taking up several times in toluene and evaporating. The residue was chromatographed on silica gel (2×50 cm column, chloroform/methanol 98:2; v:v) and the following fractions were eluted (counted from the bottom).

1. Mixed fraction comprising at least two substances, 9.4 mg, yellow;
2. TLC-uniform major product, 15 mg, yellow.

The 2nd fraction was purified on ®Sephadex LH 20 (2.5×100 cm column, methanol), and 14 mg of a yellow solid were obtained.

The $^1$H-NMR spectrum showed that the solid was a mixture comprising
80% of 3B,4B,8-tri-O-acetylurdamycin A and
20% of 3B,4B-di-O-acetylurdamycin A.

The $^1$H-NMR spectroscopic data are reproduced in Table 1.

3. Preparation of 3B-O-acetylurdamycin A 36 mg of urdamycin A were dissolved in 10 ml of acetic anhydride, and a spatula tip of anhydrous sodium acetate was added. After 2 hours, the reaction was terminated by pouring the mixture onto ice. The mixture was stirred for 4 hours and extracted 4 times with 50 ml of chloroform in each case, the combined extracts were evaporated to dryness in a rotary evaporator, and the solid residue was chromatographed on silica gel (2×50 cm column, methylene chloride/ethanol 9:1; v:v). The following fractions were obtained (counted from the bottom);

1. mixed fraction comprising two substances, 2 mg, orange;
2. TLC-uniform 3B-O-acetylurdamycin A, 21 mg, orange;
3. mixed fraction comprising two substances, 3 mg, orange;
4. unreacted urdamycin A, 12 mg, orange.

The 3B-O-acetylurdamycin obtained was purified, as was the unreacted urdamycin A, on Sephadex LH 20 (2.5×100 cm column, methanol). Besides 11 mg of urdamycin A, 20 mg of 3B-O-acetylurdamycin A (53%, 76% relative to the conversion) were obtained as an orange solid, which was characterized as follows:

$C_{45}H_{58}O_{18}$ (886.9): Calc.: C 60.82; H 6.53. Found: C 60.83; H 6.70.

Melting point 178° C (decomposition).

IR (KBr): 3430; 2980; 2935; 1727; 1660 sh; 1640; 1621; 1565 cm$^{-1}$.

UV (methanol): $\lambda_{max}$ ($\epsilon$)=425.7 (3440); 320.2 (2670); 240 sh (11710) nm.

UV (methanol/NCl): $\lambda_{max}$ ($\epsilon$)=as methanol.

UV (methanol/NaOH): $\lambda_{max}$ ($\epsilon$)=585.5 (3340); 403.7 (1520); 324.5 (5470); 228.7 (18150) nm.

$^1$H-NMR (200 MHz, CDCl$_3$): see Table 2.

CD (methanol): $\lambda_{extr.}$ ($\theta^{20} \times 10^{-3}$)=492 (−3.0); 445 (2.0).

4. Preparation of 3B,4B-di-O-acetylurdamycin A 50 g of urdamycin A were dissolved in 15 ml of acetic anhydride, and a spatula tip of anhydrous sodium acetate was added. After 16 hours, all the urdamycin A had reacted (TLC). The mixture was poured onto ice, hydrolyzed for 3 hours and extracted 3 times with 50 ml of chloroform in each case, and the combined extracts were evaporated to dryness. The residue was chromatographed on silica gel (2×30 cm column, methylene chloride/ethanol 95:5; v:v), and the following fractions were obtained (counted from the bottom):

1. mixed fraction comprising at least four substances, 15 mg, yellow;
2. TLC-uniform 3B-O-acetylurdamycin A, 12 mg, orange;
3. mixed fraction comprising at least three substances, 9 mg, orange;
4. TLC-uniform 3B,4B-di-O-acetylurdamycin A, 12 mg, orange.

Fractions 2 and 4 were purified on Sephadex LH 20 (2.5×100 cm column, methanol). 10 mg of 3B-O-acetylurdamycin A (19%) were obtained an an orange solid and 10 mg of 3B,4B-di-O-acetylurdamycin A (18%) as an orange solid. The latter was characterized as follows:

$C_{47}H_{60}O_{19}$: Calc.: C 60.71; H 6.46. Found: C 60.63; H 6.69.

Melting point: 169° C.

IR (KBr): 3440; 2980; 2935; 2870; 1745; 1735; 1658; 1640; 1621; 1563 cm$^{-1}$.

UV (methanol): $\lambda_{max}$ ($\epsilon$)=426 (4070); 320.5 (3050); 240 sh (14870) nm.

UV (methanol/HCl): $\lambda_{max}$ ($\epsilon$)=as methanol.

UV (methanol/NaOH): $\lambda_{max}$ ($\epsilon$)=581.5 (3860); 404.5 (1470); 324.7 (6500); 228.5 (22820) nm.

$^1$H-NMR (200 MHz, CDCl$_3$): see Table 2.

CD (methanol): $\lambda_{extr.}$ ($\theta^{20} \times 10^{-3}$)=466 (3.6); 406 (−8.6); 331 (29.0); 292 (10.7); 263 (−3.6); 236 sh (30.5); 226 (34.0) nm.

5. Preparation of 5′,3B,4B,4C-tetra-O-acetylurdamycin A and 4B,4C-di-O-acetylurdamycin A 60 mg of urdamycin A are dissolved in 15 ml of a mixture of acetic anhydride and pyridine (2:1) and the solution is stirred at room temperature for 7 hours. The mixture is poured onto ice and extracted 3 times with 50 ml of chloroform each time and the extract is evaporated to dryness on a rotary evaporator. Pyridine residues are removed by taking up in toluene and evaporating several times. The products are chromatographed on silica gel (preparative coated plate, 20×40 cm, chloroform/methanol-98:2) and the yellow main product is chromatographed once more on SEPHADEX LH 20 (column 50×2.5 cm, methanol). 23 mg of urdamycin pentaacetate of the formula VII are obtained as a yellow solid, $R_f$ value on silica gel thin layer plates (20×20 cm, 0.25 mm layer thickness, development distance 15 cm) of 0.83 with chloroform/methanol (4:1 by volume) or 0.91 with methylene chloride/ethanol (9:1 by volume).

$C_{53}H_{66}O_{22}$ (1055.1): Calculated: C 60.3; H 6.3. Found: C 60.4; H 6.4.

Melting point: 185° C.

IR (KBr): 3470; 1783; 1741; 1667; 1632 and 1599 cm$^{-1}$.

UV (methanol): $\lambda_{max}(\epsilon)=355$ (4300); 313 (4900). 257 (15900) nm.

(methanol/HCl): $\lambda_{max}(\epsilon)=$ as methanol.

(methanol/NaOH): $\lambda_{max}(\epsilon)=395$ sh (2600); 375 sh (3500); 327 (7400) and 253 (10400) nm.

$^1$H-NMR (200 MHz, CDCl$_3$): $\delta=0.50$ (d, J=6.5 Hz, 5C-CH$_3$); 1.18 (d, J=6.5 Hz, 5A-CH$_3$); 1.19 (d, J=6 Hz, 5B-CH$_3$); 1.25 (s, 3-CH$_3$); 1.27 (d, J=6 Hz, 6'-CH$_3$); 1.2-2,2 (complex, 13H); 2.00, 2.04, 2.06 and 2.10 (4s, 5', 3B-, 4B- and 4C-OAc); 2.36 (o, J=13.5, 2 Hz, 2B-H$_e$); 2.48 (s, 8-OAc); 2.52 and 2.80 (d. and dd., J=13 or 13 and 2 Hz, 2-H$_2$); 3.44 (dq, J=9 and 6 Hz, 5B-H); 3.48 (s, broad, 4A-H); 3.57 (s, OH*); about 3,6 (masked, 6'-H); 3.68 (dq, 6.5 and 2 Hz, 5C-H); 3.87 (dq, J=6,5 and 1 Hz, 5A-H); 4.04 (m, 4'-H); 4.06 (s, OH*); 4.56 (dd, J=10 and 2 Hz, 1B-H); 4.67 (o, J=3×about 2 Hz, 4C-H); 4,6–4,8 (masked, 2'-H); 4.74 and 4,82 (2 dd, J=9 each and 9 Hz, 5'- u. 4B-H); 4.90-5.02 (compl., 1A-H and 3B-H); 5,46 (d, J=2 Hz, 1C-H); 6.41 (d, J=10 Hz, 5-H); 6.85 (d, J=10 Hz, 6-H); 8.02 (d, J=8 Hz, 10-H) and 8.13 (d, J=8 Hz, 11-H) ppm (*)Signals disappear after replacement with CD$_3$OD CD (Methanol): $\lambda_{extr.}(\theta^{22}\times 10^{-4})=340$ (−1.4); 280 (+4.3); 250 (+3.2); 226 (+5.8) nm.

thanol 9:1; v:v). The following fractions were eluted (counted from the bottom):

1. Unreacted penta-O-acetylurdamycin A, 10 mg, yellow;
2. Mixed fraction comprising 5',3B,4B,4C-tetra-O-acetyl-urdamycin A and penta-O-acetylurdamycin A, 9 mg, orange;
3. TLC-uniform 5',3B,4B,4C-tetra-O-acetylurdamycin A, 38 mg, orange;
4. TLC-uniform 4B,4C-di-O-acetylurdamycin A, 11 mg, orange.

The 3rd and 4th fractions were purified on Sephadex LH 20 (2.5×100 cm column, methanol). The following were obtained:

31 mg (35%, 41% relative to the conversion) of 5',3B,4B,4C-tetra-O-acetylurdamycin A as an orange solid, and 10 mg (12%, 14% relative to the conversion) of 4B,4C-di-O-acetylurdamycin A as an orange solid.

(a) 5',3B,4B,4C-tetra-O-acetylurdamycin A $C_{51}H_{64}O_{21}$ (1013.1): Calc.: C 60.41; H 6.32. Found: C 60.42; H 6.50.

Melting point: 184° C.

IR (KBr): 3440; 2940; 1740; 1660 sh; 1640; 1625; 1565 cm$^{-1}$.

UV (methanol): $\lambda_{max}(\epsilon)=427.2$ (4270); 326.5 (3560); 240 sh (15970) nm.

UV (methanol/HCl): $\lambda_{max}(\epsilon)=$ as methanol.

UV (methanol/NaOH): $\lambda_{max}(\epsilon)=577$ (4020); 401.5 (1860); 323.5 (7330); 229.7 (23790) nm.

$^1$H-NMR (200 MHz, CDCl$_3$): Table 2.

CD (methanol): $\lambda_{extr.}(\theta^{20}\times 10^{-3})=500$ (−4.0); 455 (3.5); 405 (−9.0); 325 (29.6); 296 sh (20.1); 263 (−5.0); 232 (35.1) nm.

(b) 4B,4C-di-O-acetylurdamycin A $C_{47}H_{60}O_{19}$ (929.0): Calc.: C 60.71; H 6.46. Found: C 60.80; H 6.45.

Melting point: 175°–181° C.

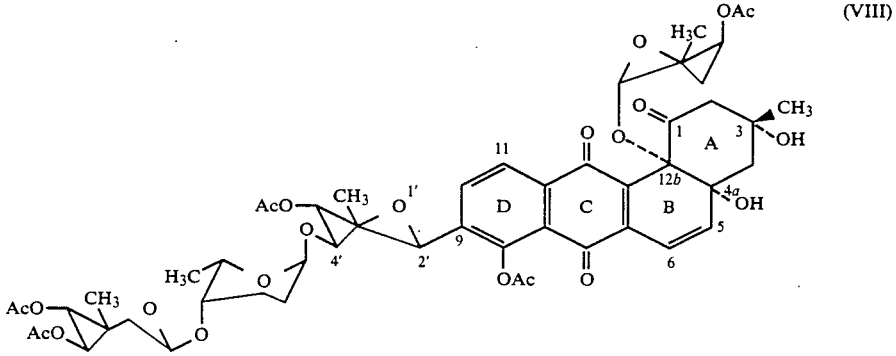

According to the procedure described immediately, above Example 14, were dissolved in 7 ml of water and 10 ml of methanol, and 3.5 ml of a saturated sodium carbonate solution were added at 25° C. The color of the solution immdiately changed to deep blue. The mixture was stirred for 10 minutes under a nitrogen atmosphere, and the reaction was terminated by adding acetic anhydride (color change). The solution was poured onto ice and extracted five times with 30 ml of chloroform in each case. The combined extracts were subsequently evaporated to dryness in a rotary evaporator, and the solid residue was chromatographed on silica gel (2.5×50 cm column, methylene chloride/e-

IR (KBr): 3450; 1740; 1660; 1640; 1622; 1565 cm$^{-1}$.

UV (methanol): $\lambda_{max}(\epsilon)=427$ (4100); 326 (3900) nm.

UV (methanol/HCl): $\lambda_{max}(\epsilon)=$ as methanol.

UV (methanol/NaOH); $\lambda_{max}(\epsilon)=585$ (33700); 406 (1600); 324 (8300); 228 (21700) nm.

$^1$H-NMR (200 MHz, CDCl$_3$): Table 2.

CD (methanol): $\lambda_{extr.}(\theta^{20}\times 10^{-3})=500$ (=4.8); 455 (5.7); 408 (−3.8); 325 (23.5); 295 sh (16.8); 263 (−4.3); 235 (31.1) nm.

TABLE 1

<sup>1</sup>H-NMR signals of the acetates (1) and (2) in CDCl<sub>3</sub>
(δ in ppm relative to internal TMS, J in Hz)

|  | (1) | (2) |
|---|---|---|
| 2-H$_a$ | 2.53 (d, 13) | 2,52 (d, 13) |
| 2-H$_e$ | 2.81 (d, 13;2) | 2.79 (dd, 13;2) |
| 3-CH$_3$ | 1.25 (s) | 1.23 (s) |
| 4-H$_2$ | 1.2–2.2 (complex) | 1.3–2.0 (complex) |
| 5-H | 6.01 (d, 10) | 6.38 (d, 10) |
| 6-H | 6.66 (d, 10) | 6.84 (d, 10) |
| 10-H | 8.13 (d, 8) | 8.10 (d, 8) |
| 11-H | 8.02 (d, 8) | 8.01 (d, 8) |
| 2'-H | 4.95 (covered) | 4.89 (dd, 10;2) |
| 3'-H$_2$ | 1.2–2.2 (complex) | 1.3–2.0 (complex) |
| 4'-H | 3.98 (m) | 3.4–3.8 (complex) |
| 5'-H | 4.73 (dd, 9;9) | 3.17 (dd, 9;9) |
| 6'-H | 3.61 (dq, 9;6) | 3.4–3.8 (complex) |
| 6'-CH$_3$ | 1.27 (d, 6) | 1.41 (d, 6) |
| 1A-H | 4.91 (d) | 5.01 (s, broad) |
| 2A-H$_2$ | 1,2–2.2 (complex) | 1.3–2.0 (complex) |
| 3A-H$_2$ | 1.2–2.2 (complex) | 1.3–2.0 (complex) |
| 4A-H | 3.48 (s,broad) | 3.4–3.8 (complex) |
| 5A-H | 3.88 (dq, 6.5;2) | 4.12 (dq, 6.5;2) |
| 5A-CH$_3$ | 1.13 (d, 6.5) | 1.18 (d, 6) |
| 1B-H | 4.57 (dd, 9.5;2) | 4.57 (dd, 10;2) |
| 2B-H$_a$ | 1.2–2.2 (complex) | 2.18 (ddd, 13;12;12) |
| 2B-H$_a$ | 2.39 (ddd, 13;5;2) | 2.38 (ddd, 13;5;2) |
| 3B-H | 4.95 (m) | 4.75 (m) |
| 4B-H | 4.81 (dd, 9;9) | 4.48 (dd, 9;9) |
| 5B-H | 3.44 (dq, 9;6) | 3.4–3.8 (complex) |
| 5B-CH$_3$ | 1.14 (d, 6) | 1.21 (d, 6) |
| 1C-H | 5.44 (s, broad) | 5.41 (s, broad) |
| 2C-H$_2$ | 1.2–2.2 (complex) | 1.3–2.0 (complex) |
| 3C-H$_2$ | 1.2–2.2 (complex) | 1.3–2.0 (complex) |
| 4C-H | 3.49 (s, broad) | 3.4–3.8 (complex) |
| 5C-H | 3.69 (dq, 6.5;2) | 3.67 (dq, 6.5;2) |
| 5C-CH$_3$ | 0.57 (d, 6.5) | 0.57 (d, 6.5) |

5',3B,4B,8-tetra-O-acetylurdamycin A (1)
3B,4B,8-tri-O-acetylurdamycin A (2)

TABLE 6

<sup>1</sup>H-NMR signals of the acetates (3) to (6) in CDCl<sub>3</sub> (δ in ppm relative to internal TMS, J in Hz)

|  | (3) | (4) | (5) | (6) |
|---|---|---|---|---|
| 2-H$_a$ | 2.51 (d, 13) | 2.52 (d, 13) | 2.42 (d, 13) | 2.51 (d, 13) |
| 2-H$_e$ | 2.79 (dd, 13;2.5) | 2.79 (dd, 13;2) | 2.82 (dd, 13;2) | 2.82 (dd, 13;2) |
| 3-CH$_3$ | 1.24 (s) | 1.23 (s) | 1.24 (s) | 1.25 (s) |
| 4-H$_2$ | 1.4–2.0 (complex) | 1.3–2.0 (complex) | 1.2–2.2 (complex) | 1.2–2.0 (complex) |
| 5-H | 6.43 (d, 10) | 6.24 (d, 10) | 6.45 (d, 10) | 6.46 (d, 10) |
| 6-H | 6.91 (d, 10) | 6.92 (d,10) | 6.93 (d, 10) | 6.95 (d, 10) |
| 10-H | 7.95 (d, 8) | 7.94 (d, 8) | 7.95 (d, 8) | 7.96 (d, 8) |
| 11-H | 7.70 (d, 8) | 7.70 (d, 8) | 7.72 (d, 8) | 7.72 (d, 8) |
| 2'-H | 4.88 (dd, 11.5;2) | 4.88(dd, 10;2) | 4.92 (dd, 11;2) | 4.91 (dd, 10;2) |
| 3'-H$_a$ | 1.4–2.0 (complex) | 1.3–2.0 (complex) | 1.2–2.2 (complex) | 1.2–2.0(complex) |
| 3'-H$_e$ | 2.18 (ddd, 13;5;2) | 2.18 (ddd, 13;5;2) | 2.32 (ddd, 13;5;2) | 2.36 (ddd, 13;5;2) |
| 4'-H | 3.70 (m) | 3.4–3.6 (complex) | 4.01 (m) | 4.00 (m) |
| 5'-H | 3.15 (dd, 9;9) | 3.17 (dd, 9;9) | 3.10 (ddd, 9;9;6) | 4.50 (dd, 9;9) |
| 6'-H | 3.56 (m) | 3.4–3.6 (complex) | 3.61 (dq, 9;6) | 3.6–3.8 (complex) |
| 6'-CH$_3$ | 1.43 (d, 6) | 1.41 (d, 6) | 1.30 (d, 6) | 1.30 (d, 6) |
| 1A-H | 5.02 (d, 2) | 5.03 (d, 2) | 4.99 (d, 2) | 4.93 (d, 2) |
| 2A-H$_2$ | 1.4–2.0 (complex) | 1.3–2.0 (complex) | 1.2–2.2 (complex) | 1.2–2.0 (complex) |
| 3A-H$_2$ | 1.4–2.0 (complex) | 1.3–2.0 (complex) | 1.2–2.2 (complex) | 1.2–2.0 (complex) |
| 4A-H | 3.44 (s) | 3.4–3.8 (complex) | 3.49 (s) | 3.60 (s) |
| 5A-H | 4.12 (dq, 6.5;2) | 4.12 (dq, 6.5;2) | 3.89 (6.5;2) | 3.91 (dq, 6.5;2) |
| 5A-CH$_3$ | 1.21 (d, 6.5) | 1.18 (d, 6) | 1.20 (d, 6) | 1.18 (d, 6) |
| 1B-H | 4.55 (dd, 10;2) | 4.57 (dd, 10;2) | 4.52 (dd, 10;2) | 4.57 (dd, 9;2) |
| 2B-H$_a$ | 1.4–2.0 (complex) | 1.3–2.0 (complex) | 1.2–2.2 (complex) | 2.16 (covered) |
| 2B-H$_e$ | 2.39 (ddd, 13;5;2) | 2.38 (ddd, 13;5;2) | 2.62 (sss, 13;5;2) | 2.63 (ddd, 13;5;2) |
| 3B-H | 4.79 (ddd, 12;8;5) | 4.97 (m) | 3.5–3.8 (complex) | 4.8 (m) |
| 4B-H | 3.44 (dd, 9;9) | 4.74 (dd, 9;9) | 4.83 (dd, 9;9) | 4.79 (dd, 9.5;9.5) |
| 5B-H | 3.29 (m) | 3.4–3.8 (complex) | 3.27 (dq, 9;6) | 3.30 (dq, 9;6) |
| 5B-CH$_3$ | 1.33 (d, 6) | 1.21 (d, 6) | 1.28 (d, 6) | 1.20 (d, 6) |
| 1C-H | 5.41 (s) | 5.40 (s) | 5.47 (s) | 5.60 (s) |
| 2C-H$_2$ | 1.4–2.0 (complex) | 1.3–2.0 (complex) | 1.2–2.2 (complex) | 1.2–2.2 (complex) |
| 3C-H$_2$ | 1.4–2.0 (complex) | 1.3–2.0 (complex) | 1.2–2.2 (complex) | 1.2–2.0 (complex) |
| 4C-H | 3.31 (s) | 3.4–3.8 (complex) | 4.70 (o, 3x2) | 4.67 (s) |
| 5C-H | 3.67 (dq, 6.5;2) | 3.67 (dq, 6.5;2) | 3.69 (d, 6.5;2) | 3.6–3.8 (complex) |
| 5C-CH$_3$ | 0.58 (d, 6.5) | 0.57 (d, 6.5) | 0.52 (d, 6.5) | 0.53 (d, 6.5) |

3B-O-acetylurdamycin A (3)
3B,4B-di-O-acetylurdamycin A (4)
4B,4C,di-O-acetylurdamycin A (5)
5',3B,4B,4C-tetra-O-acetylurdamycin A (6)

6. In vitro test for cytostatic activity

The experiment was carried out in accordance with the process of Hamburger and Salmon [New Engl. J. Med. 298, 1321–1327 (1978)]. The medium was replaced by McCoy 5A, and the number of cells was reduced to $5 \times 10^2$ cells/plate.

(a) Action of L 1210 leukemia cells in the continuous experiment

A continuous incubation of cells with various concentrations of the test substance from Examples 1 to 5 and 5',3B,4B,4C,8-penta-O-acetylurdamycin A was carried out. The compounds to be tested were applied to the agar plates before plating-out the cell cultures. The cell cultures then grew for 5 to 7 days in the incubation in an atmosphere of 5% of CO$_2$, 20% of O$_2$ and 95% relative atmospheric humidity at 37° C. After this time, the number of cell colonies having a diameter from 60 μm was determined (in %) relative to the number of cell colonies which had grown in comparison without test substance.

(b) Action on L 1210 leukemia cells in the 1-hour experiment

In the test, the cells were incubated at 37° C. for 1 hour at various concentrations of the test substance. The cells were then washed twice with McCoy 5A solution and subsequently applied to agar plates in accordance with the method of Hamburger and Salmon. The cells were subsequently cultivated as described above, and the number of cell colonies was determined (evaluation as in a).

The $IC_{50}$ value for continuous and 1-hour incubation was determined from the dose/action curve.

(c) Proliferation experiment

L 1210 tumor cells at the exponential growth phase ($5 \times 10^3$ cells/ml, Roswell Park Memorial Institute (RPMI) medium) were incubated in a microtiter plate with 26 recesses for a period of 72 hours at 37° C., 5% of $CO_2$ and 95% relative atmospheric humidity and various concentrations of the test substances from Examples 1 to 5 and also 5',3B,4B,4C,8-penta-O-acetylurdamycin A. After 65 hours, 50 μl of 3-(4,5-dimethylthiazol-2-yl)-2,5-diphenyltetrazolium bromide (MTT) (2.5 mg/ml of MIT in phosphate buffer saline (PBS)) were added. The MTT was reduced by living cells into the red, water-insoluble dyestuff formazan. After a further 7 hours, the supernatant medium was carefully removed. Formazan was dissolved by adding 100 μl of dimethyl sulfoxide per recess and subsequently shaking gently. The extinction of each recess was determined using a multisan 340 CC photometer (Messrs. Flow) at 491 nm. The results were determined from the extinction ratio of cells with test substance to cells without test substance.

In all cases, the experiments were carried out 4 times. The deviation in the results was less than 15%.

The results are collated in the following table:

| Test substance | Proliferation test | $IC_{50}$ (μg/ml) Strain test continuous | 1 hour |
|---|---|---|---|
| Penta-O-acetylu. A | <1 | 0.042 | 0.12 |
| 5',3B,4B,8-Tetra-O-acetylu. A | <1 | 0.075 | |
| 5',3B,4B,4C-Tetra-O-acetylu. A | <1 | 0.078 | 0.25 |
| 4B,4C-Di-O-acetylu. A | <1 | 0.13 | 0.85 |
| 3B,4B-Di-O-acetylu. A | <1 | 0.11 | 0.35 |
| 3B,4B,8-Tri-O-acetylu. A | <1 | 0.4 | 1.1 |
| 3B-O-Acetylurdamycin A | <1 | 0.28 | 2.2 |
| 3B-O-Octanoylurdamycin A | <1 | n.d. | 0.26 |
| 4B-O-Octanoylurdamycin A | <1 | n.d. | 0.09 | n.d. = not determined

We claim:

1. A compound of the formula I

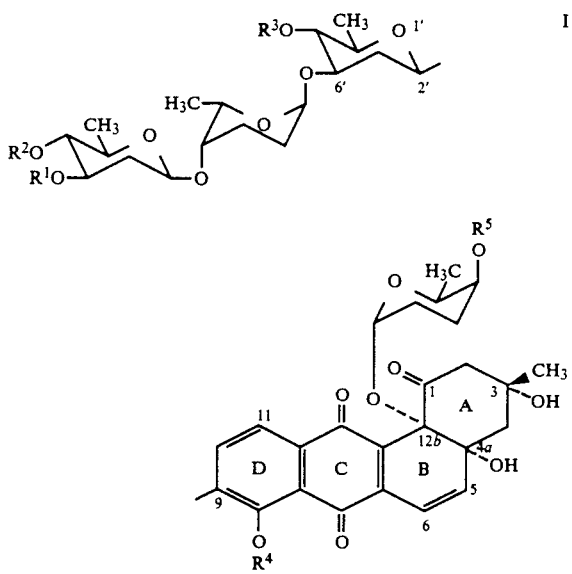

in which $R^1$ to $R^5$, independently of one another, are hydrogen or a ($C_1$ to $C_{18}$)-acyl group, wherein at least one of $R_1$ to $R_5$ are acyl, apart from 5',3B,4B,4C,8-penta-O-acetylurdamycin A.

2. A compound as claimed in claim 1, wherein $R^1$ to $R^5$, independently of one another, denote hydrogen or a ($C_1$ to $C_{10}$)-acyl group.

3. A compound as claimed in claim 2, wherein $R^1$ to $R^5$, independently of one another, denote hydrogen or an acetyl group or an octanoyl group.

4. A method of treating an animal or human suffering from leukemia comprising administering to said animal or human an amount of the compound of formula I as claimed in claim 1 effective to inhibit the growth of leukemia cells exposed to said compound.

5. A pharmaceutical composition comprising one or more pharmaceutically acceptable excipients and an amount of the compound of formula I as claimed in claim 1 effective to treat or inhibit bacterial infections or leukemia cells in an animal or patient to whom said composition is administered.

* * * * *